(12) United States Patent
Kvam et al.

(10) Patent No.: US 10,450,345 B2
(45) Date of Patent: Oct. 22, 2019

(54) METHOD OF ISOLATION OF POLYPEPTIDE-APTAMER-POLYMER CONJUGATES

(71) Applicant: General Electric Company, Schenectady, NY (US)

(72) Inventors: Erik Leeming Kvam, Albany, NY (US); Bruce Allan Hay, Niskayuna, NY (US); Ernest William Kovacs, San Diego, CA (US)

(73) Assignee: General Electric Company, Schenectady, NY (US)

( * ) Notice: Subject to any disclaimer, the term of this patent is extended or adjusted under 35 U.S.C. 154(b) by 187 days.

(21) Appl. No.: 15/619,148

(22) Filed: Jun. 9, 2017

(65) Prior Publication Data
US 2018/0354987 A1  Dec. 13, 2018

(51) Int. Cl.
| | | |
|---|---|---|
| *C07K 1/36* | (2006.01) | |
| *C08L 71/02* | (2006.01) | |
| *C07K 16/00* | (2006.01) | |
| *B01D 11/04* | (2006.01) | |

(Continued)

(52) U.S. Cl.
CPC ............ *C07K 1/36* (2013.01); *B01D 11/0492* (2013.01); *B01D 15/3804* (2013.01);
(Continued)

(58) Field of Classification Search
CPC .......... C07K 1/36; C07K 1/145; C07K 16/00; C07K 1/14; C07K 1/22; B01D 11/0492;
(Continued)

(56) References Cited

U.S. PATENT DOCUMENTS 3,780,138 A * 12/1973 Hassell et al. ............ C08C 2/04
528/483
5,998,588 A * 12/1999 Hoffman .................. B82Y 5/00
424/178.1

(Continued)

OTHER PUBLICATIONS

Mazzola, Priscila G., et al.; "Liquid-Liquid Extraction of Bio molecules: An Overview and Update of The Main Techniques", Journal of Chemical Technology and Biotechnology, vol. 83, Issue 2, pp. 143-157, Feb. 2008.

(Continued)

*Primary Examiner* — Joseph W Drodge
(74) *Attorney, Agent, or Firm* — Eversheds Sutherland (US) LLP (57) ABSTRACT

A method for purification of a target in a solution includes providing a target in a solution, the solution comprising one or more contaminants, providing a polymer conjugate in the solution, wherein the polymer conjugate is configured to specifically bind the target, incubating the solution at a first temperature to facilitate binding of the polymer conjugate to the target, providing an environmentally-responsive block copolymer in the solution, wherein the environmentally-responsive block copolymer comprises one or more of an ethylene oxide (EO), a propylene oxide (PO), or an EO/PO block copolymer, and heating the solution comprising the environmentally-responsive block copolymer and the polymer conjugate bound to the target at a second temperature to initiate a liquid-liquid phase separation, wherein the liquid-liquid phase separation produces an aqueous phase and a liquid polymer phase, and wherein the liquid polymer phase comprises the polymer conjugate bound to the target.

18 Claims, 7 Drawing Sheets

(51) Int. Cl.
*C12N 15/11* (2006.01)
*B01D 17/02* (2006.01)
*C07K 1/14* (2006.01)
*B01J 20/26* (2006.01)
*B01D 15/38* (2006.01)
*C12N 15/115* (2010.01)

(52) U.S. Cl.
CPC ........ *B01D 17/0217* (2013.01); *B01J 20/264* (2013.01); *C07K 1/145* (2013.01); *C07K 16/00* (2013.01); *C08L 71/02* (2013.01); *B01D 11/0488* (2013.01); *C12N 15/115* (2013.01); *C12N 2310/16* (2013.01); *C12N 2310/351* (2013.01)

(58) Field of Classification Search
CPC .. B01D 15/3876; B01D 11/02; B01D 11/028; B01D 11/0288; B01D 11/04; B01D 11/0488; B01D 15/38; B01D 15/3804; B01D 15/3861; B01D 17/02; B01D 17/0217; C08L 71/02; C12N 15/115; C12N 2310/16; C12N 2310/351; C12N 15/1003; C12N 15/1006; C12N 15/101; B01J 20/26; B01J 20/264; B01J 2220/4812; B01J 2220/4856; C12M 47/02; C12M 47/12; C12M 47/20
See application file for complete search history.

(56) References Cited

U.S. PATENT DOCUMENTS

| | | | |
|---|---|---|---|
| 6,258,275 B1 | 7/2001 | Freitag et al. | |
| 6,454,950 B1 | 9/2002 | Tjerneld et al. | |
| 7,897,684 B2 * | 3/2011 | Bazan | C08G 61/02 428/690 |
| 8,268,915 B2 | 9/2012 | Johansson et al. | |
| 8,669,055 B2 * | 3/2014 | Bazan | C12Q 1/6818 422/82.07 |
| 9,115,181 B2 | 8/2015 | Van Alstine et al. | |
| 2004/0191324 A1 | 9/2004 | Ramstack | |
| 2005/0175702 A1 * | 8/2005 | Muller-Schulte | A61K 41/00 424/486 |
| 2007/0048248 A1 | 3/2007 | Benedict et al. | |
| 2008/0255027 A1 * | 10/2008 | Moya | C07K 1/30 514/1.1 |
| 2009/0286955 A1 | 11/2009 | Hatala et al. | |
| 2009/0294735 A1 | 12/2009 | Yoshida et al. | |
| 2010/0063179 A1 | 3/2010 | Atkinson et al. | |
| 2017/0253673 A1 * | 9/2017 | Kent | C07K 17/08 |

OTHER PUBLICATIONS

Ferreira, Luisa, et al.; "Structural Features Important for Differences in Protein Partitioning in Aqueous Dextran-polyethylene Glycol Two-phase Systems of Different Ionic Compositions", Biochimica et Biophysica Acta, vol. 1844, pp. 694-704, Jan. 30, 2014.

Burmistrova, Anna, et al.; "The Effect of Co-Monomer Content on the Swelling/Shrinking and Mechanical Behaviour of Individually Adsorbed PNIPAM Microgel Particles", Polymers, vol. 3, pp. 1575-1590, 2011.

Averick, Saadyah, et al.; "Solid-Phase Incorporation of an ATRP Initiator for Polymer-DNA Biohybrids", Angew. Chem. Int. Ed., vol. 53, Issue 10, pp. 2739-2744, Mar. 3, 2014.

* cited by examiner

| CO - SOLVENT | CLOUD POINT 1% IN PBS,°C | 2 LIQUID PHASES 20% IN PBS WITH 25mg/ml PNIPAM, 40°C |
| --- | --- | --- |
| PLURONIC L121 | <10 | NO,PPT |
| PLURONIC L64 | <10 | NO,PPT |
| PLURONIC F127 | <10 | NO,PPT |
| PPG1000-Obu | <10 | NO,PPT |
| PPG2500-Obu | <10 | NO,PPT |
| BRIJ L4 | <10 | NO,PPT |
| BRIJ C10 | <10 | NO,PPT |
| PPG 2000 | 16.4 | NO,PPT |
| PLURONIC L81 | 19.1 | NO,PPT |
| PLURONIC 31R1 | 21.2 | NO,PPT |
| PLURONIC L61 | 21.6 | NO,PPT |
| PPG340-Obu | 23.9 | NO,PPT |
| PPG 1000 | 31.5 | YES |
| PLURONIC L31 | 36 | YES |
| PPG 725 | 39.5 | YES |
| PLURONIC 17R4 | 40.2 | YES |
| PLURONIC17R4:10R5 3:1 | 42.5 | NO,PPT |
| PLURONIC17R4:10R5 1:1 | 44.5 | NO,PPT |
| PLURONIC 10R5 | 65 | NO,PPT |
| PPG 425 | >80 | NO,PPT |
| PPG 400 | >80 | NO,PPT |
| PPG 2050 | >80 | NO,PPT |
| PEG 10,000 | >80 | NO,PPT |

METHOD OF ISOLATION OF POLYPEPTIDE-APTAMER-POLYMER CONJUGATES

BACKGROUND

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

The subject matter disclosed herein relates generally to methods for separating and purifying biomolecules, and more specifically, to methods of liquid-liquid extraction isolation of polypeptides using aptamer-polymer conjugates.

A number of currently approved biopharmaceuticals are polypeptides (e.g., antibodies). Biopharmaceutical synthesis in production reactors (e.g. cell-based fermentation) is typically followed by downstream processing and purification to remove contaminants that are unwanted in the formulated biopharmaceutical. Contaminants may include but are not limited to host cell proteins, host cell DNA, intact cells or cell debris, endotoxins (in the case of bacterial production systems), viruses (in the case of mammalian production systems), misfolded proteins and aggregates, and components that leach from chromatographic media. Examples of purification techniques to separate a target polypeptide product from contaminants include centrifugation, filtration, and column-based chromatography. These techniques may include difficult process steps that lead to greater opportunities for system breakdown. There exists a need for improvement in purification, ideally selective-purification, using methods with simpler process steps. Also, it is desirable to affinity-purify a product, or selectively remove a contaminant, under high flow capacities, such as what might be experienced in continuous purification processes.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In a first embodiment, a method for purification of a target in a solution includes providing a target in a solution, the solution comprising one or more contaminants, providing a polymer conjugate in the solution, wherein the polymer conjugate is configured to specifically bind the target, incubating the solution at a first temperature to facilitate binding of the polymer conjugate to the target, providing an environmentally-responsive block copolymer in the solution, wherein the environmentally-responsive block copolymer comprises one or more of an ethylene oxide (EO), a propylene oxide (PO), or an EO/PO block copolymer, and heating the solution comprising the environmentally-responsive block copolymer and the polymer conjugate bound to the target at a second temperature to initiate a liquid-liquid phase separation, wherein the liquid-liquid phase separation produces an aqueous phase and a liquid polymer phase, and wherein the liquid polymer phase comprises the polymer conjugate bound to the target.

In a second embodiment, a method for selective purification of a target in a solution includes binding a target to an aptamer of a polymer-aptamer conjugate in a solution, wherein the aptamer of the polymer-aptamer conjugate is configured to specifically bind the target, and separating the solution into two liquid phases using a thermoresponsive block copolymer, wherein the thermorepsonsive block copolymer is one of an ethylene oxide (EO), a propylene oxide (PO), or an EO/PO block copolymer, wherein the thermoresponsive block copolymer has a cloud point between 25° C. and 41° C., and wherein the two liquid phases comprise an aqueous phase and a liquid polymer phase, and wherein the liquid polymer phase comprises the target bound to the polymer-aptamer conjugate.

In a third embodiment, a method for selective purification of a target in a solution includes adding a polymer-aptamer conjugate to a solution comprising a target, wherein the polymer-aptamer conjugate is configured to bind the target, wherein the polymer of the polymer-aptamer conjugate comprises a thermoresponsive polymer having a first cloud point, and wherein the aptamer of the polymer-aptamer conjugate comprises a DNA aptamer, incubating the solution at a first temperature to facilitate binding of the polymer-aptamer conjugate to the target, adding a thermoresponsive block copolymer to the solution, wherein the thermoresponsive block copolymer is one of an ethylene oxide (EO), a propylene oxide (PO), or an EO/PO block copolymer and has a second cloud point between 25° C. and 41° C., and heating the solution at a second temperature to initiate a first liquid-liquid phase separation, wherein the second temperature is higher than the first temperature, wherein the first liquid-liquid phase separation produces a first aqueous phase and a first liquid polymer phase, wherein the first aqueous phase comprises unbound species, and wherein the first liquid polymer phase comprises the target bound to the polymer-aptamer conjugate.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Biopharmaceuticals may be pharmaceutical drug products manufactured in, extracted from, or synthesized from biological sources. As noted above, synthesis of biopharmaceuticals, such as antibodies, may involve production in cell-based production reactors (e.g., bioreactors or fermentation vessels). This production is typically followed by downstream processing and purification to remove contaminants, such as host cell proteins and host cell DNA, intact cells or cell debris, endotoxins (in the case of bacterial production systems), viruses (in the case of mammalian production systems), misfolded proteins and aggregates, and components that leach from chromatographic media, that are unwanted in the formulated biopharmaceuticals. Examples of purification processes include filtration, centrifugation, and column-based chromatography, which may be difficult to optimize or perform or otherwise elicit system breakdown or fouling, such as at high flow capacities. A simpler purification technique with few opportunities for breakdown or fouling and relatively high selectivity for a target polypeptide may enable and increase the efficiency of biopharmaceutical production in industrial settings.

Generally, the disclosed embodiments are directed toward methods of liquid-liquid extraction isolation of polypeptides using aptamer-polymer conjugates that may be used in biopharmaceutical processing and purification. In some embodiments, the disclosed method may include the addition of a thermoresponsive polymer and a DNA aptamer to the target polypeptide (e.g., antibody) product in a cell-based biopharmaceutical bioreactor. This may enable the thermoresponsive polymer and the DNA aptamer conjugate to bind to the target polypeptide, thus enabling an increase in the selectivity of the isolation method for the target productivity. In some embodiments, the isolation method may further include addition of a thermoresponsive block co-polymer (e.g., pluronic) as an organic co-solvent to separate the solution into two liquid phases, an aqueous phase and a liquid polymeric phase. The cloud point of the thermoresponsive block co-polymer may be within a particular range, thus enabling the bioseparation of the aqueous phase containing the contaminants and the liquid polymeric phase containing the target polypeptide. This bioseparation may enable the target polypeptide to be separated, extracted, and eluted using a simple liquid extraction technique. The disclosed liquid-liquid extraction isolation method may, thus, enable an increase in the efficiency and selectivity of purification of target biopharmaceutical products from solution. In other embodiments, the disclosed method may target polypeptide contaminants for selective removal. This may enable higher purity of the desired purification target by reducing or eliminating background within a purification process.

Figure 1:
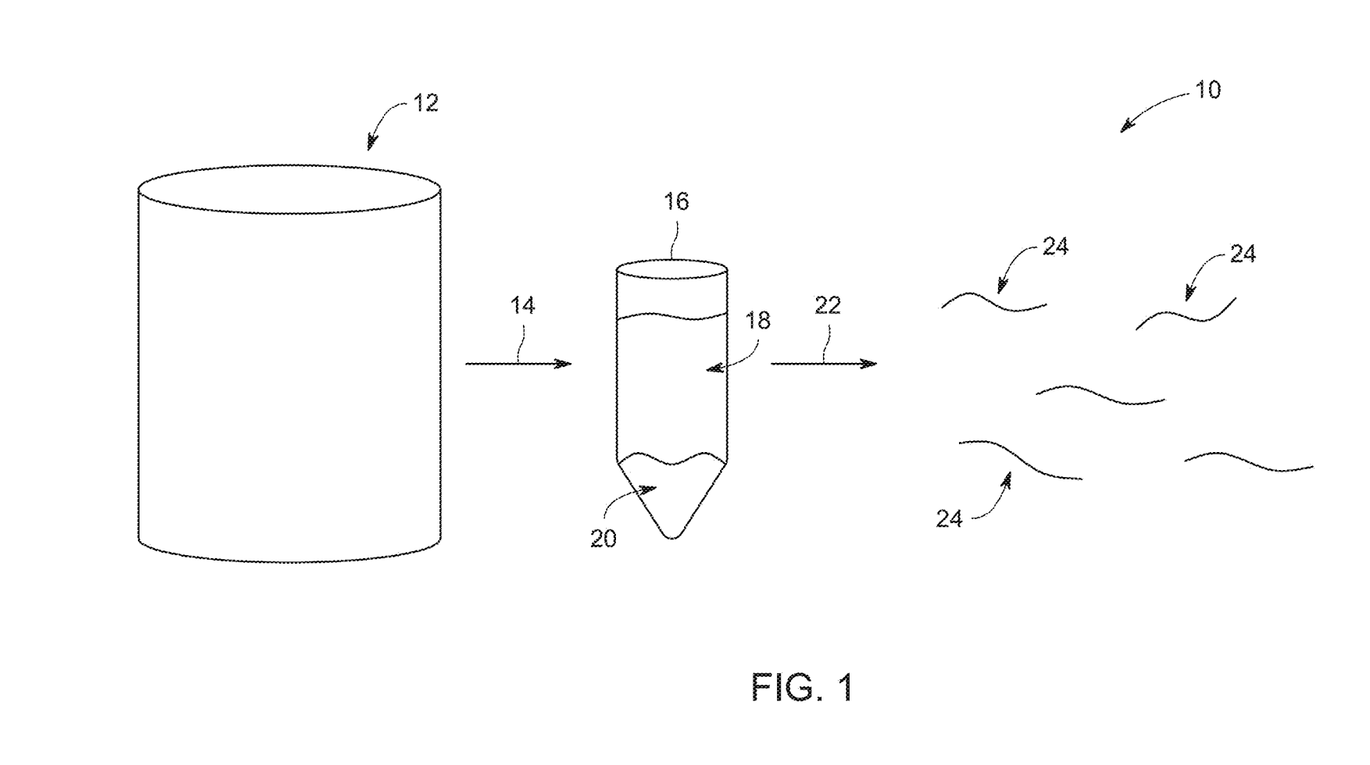
FIG. 1 is a schematic diagram of an embodiment of a method for isolating targets using aptamer-polymer conjugates, in accordance with aspects of the present disclosure.

To illustrate, FIG. 1 shows a schematic diagram of an embodiment of a method 10 for isolating polypeptide-aptamer-conjugates, and thus target polypeptides (e.g., antibodies), from contaminants of the target polypeptide production process. Target polypeptide 24 synthesis may take place within a target polypeptide production container 12 (e.g., cell based production reactor). The container 12 may contain biological cells in which the target polypeptide 24 may be manufactured in and/or extracted from. During or upon the completion of production of the target polypeptide 24 within the container 12, the production product may be extracted from the container 12 and run through a bioseparation process 14. The bioseparation process 14 may occur within a reaction vessel 16. The bioseparation process 14 may include a liquid-liquid extraction technique, discussed in greater detail with reference to FIG. 2, to separate a mixture of the target polypeptide 24 and other solutions into an aqueous phase 18 (e.g., aqueous supernatant) that may contain any unwanted contaminants and a liquid polymer phase 20 that may contain the target polypeptide 24. Next, the liquid polymer phase 20 may be extracted and processed in step 22 such that the target polypeptide 24 is eluted and isolated.

Figure 2:
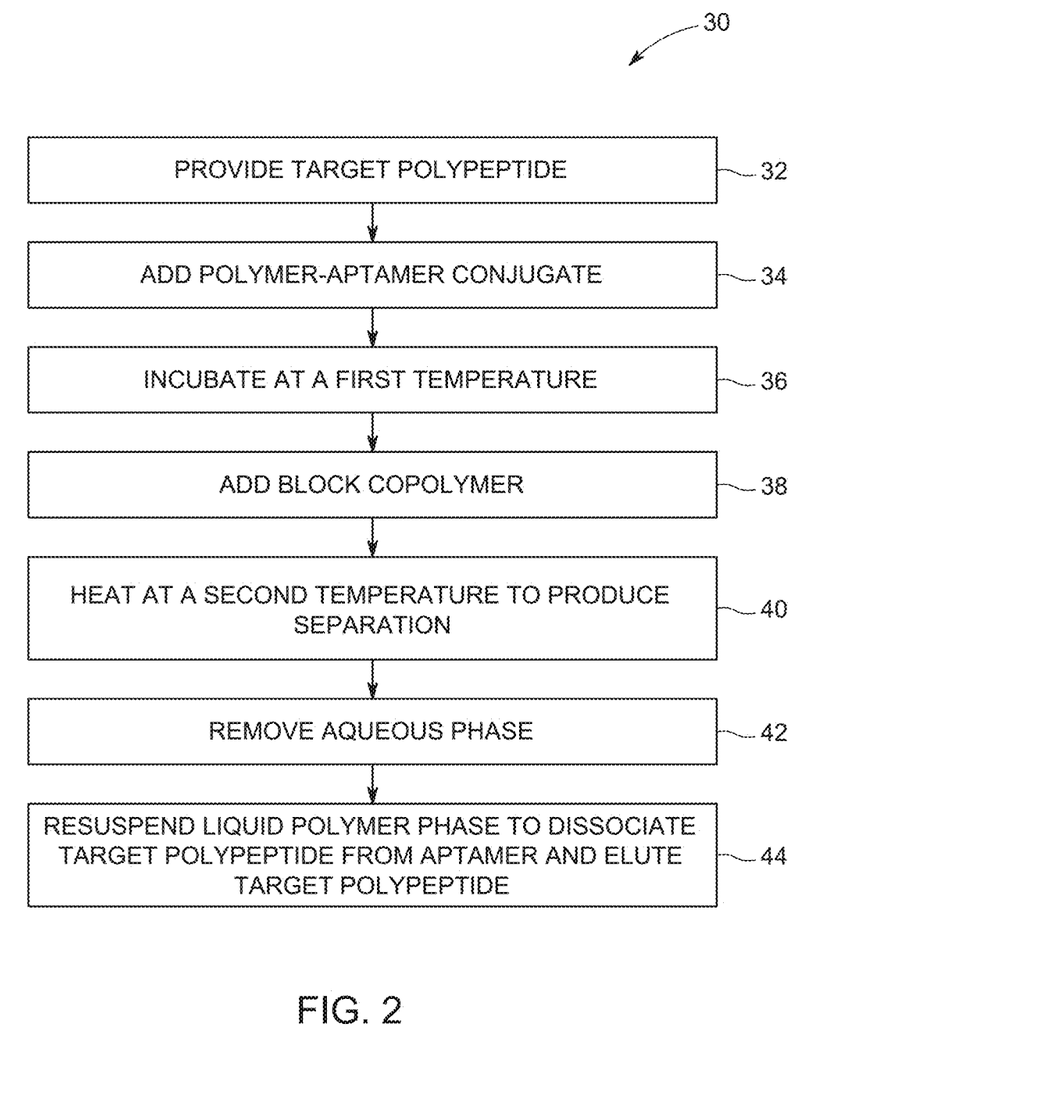
FIG. 2 is a flow diagram of an embodiment of a method for isolating targets using aptamer-polymer conjugates, in accordance with aspects of the present disclosure.

FIG. 2 is a flow diagram of an embodiment of a method 30 for isolating polypeptides using aptamer-polymer conjugates, and thus enables selective-purification of target polypeptides (e.g., antibodies) from contaminants of the target polypeptide production process. At a first step, a target polypeptide 24 may be provided (block 32). In some embodiments, the target polypeptide may be DNA, a biotherapeutic protein (e.g., enzyme, antibody, peptide hormone, clotting factor), a contaminant in the solution (e.g., host cell protein, host cell nucleic acid), or DNA associated with a solution contaminant (e.g., histone-associated DNA). For example, the target polypeptide 24 may be an antibody (e.g., IgG) produced in a cell-based production reactor (e.g., container 12). However, the target polypeptide 24 may also be added to a host cell feedstock by spiking. In certain embodiments, the biological cells used for production of the target polypeptide 24 may be Chinese Hamster Ovary (CHO) Cells, as CHO cells are a mammalian cell line commonly used for mass production of biopharmaceuticals (e.g., target polypeptides). However, the biological cells within the container 12 may be any host cells (e.g., mammalian cells, bacterial cells) suitable for producing the target polypeptide 24. Thus, at step 32, the target polypeptide 24 may be secreted and provided with cell waste, which may include contaminants that are unwanted in the target polypeptide 24 or formulated biopharmaceutical. The contaminants of the production of the target polypeptide 24 may be removed through downstream processing, such as the method 30 for isolating polypeptides using aptamer-polymer conjugates.

Next, a polymer-aptamer conjugate may be added to or otherwise contacted with the production solution (e.g., target polypeptide and host cell waste) (block 34). The aptamer may be an oligonucleotide or peptide molecule that binds a specific target molecule, here the target polypeptide 24. The aptamer may include DNA, RNA, or mixtures of DNA and RNA sequences. In some embodiments, the aptamer may be a DNA aptamer. In one example, the aptamer may be IgG aptamer for binding IgG as the target polypeptide 24. In some embodiments, the aptamer may be a mixture of two or more aptamers to bind a desired number of target polypeptides in a single reaction. The polymer and aptamer may be conjugated via direct or indirect methods of conjugation.

The polymer of the polymer-aptamer conjugate may be a thermoresponsive polymer (e.g., an environmentally-responsive polymer), such that the polymer exhibits a reversible change in its physical properties with temperature. The thermoresponsive property of the polymer may enable the liquid-liquid bioseparation to occur downstream in the process of the method 30. The thermoresponsive characteristic of the polymer may be described using a lower critical solution temperature (LCST) or a cloud point. The LCST is the temperature below which the polymer may be miscible in solution. In this manner, at temperatures at or above the LCST, partial liquid miscibility of the polymer may occur. The cloud point is the temperature at which the polymer in solution may begin to phase-separate, thus having a cloudy appearance in solution phase. In some embodiments, the thermoresponsive polymer that may be used in the polymer-aptamer conjugate may be poly(N-isopropylacrylamide) (pNIPAM). The LCST or cloud point of 32° C. for pNIPAM makes it preferable for use in biological systems. The LCST of approximately 32° C. is in a range compatible with the thermostability of the majority of biomolecules (e.g., less than 45° C.). However, alternative thermoresponsive polymers and combinations thereof are also contemplated within the scope of embodiments provided herein. The pNIPAM (e.g., polymer) used may range in molecular weight from large (e.g., greater than 28 kDa) to small (e.g., 10-28 kDa) to oligomeric (e.g., less than 10 kDa). In certain embodiments, the polymer in the polymer-aptamer conjugate may be selected independently of molecular weight and may be selected based on a desired cloud point. Recovery using polymer-aptamer conjugates may enable an increase in the isolation efficiency of the purification process, as the polymer-aptamer conjugate is highly sensitive and specific for the target polypeptide 24. In some embodiments, the target polypeptide is an undesirable contaminant species.

Next, the solution containing the target polypeptide 24, the contaminants, and the polymer-aptamer conjugate may be incubated to enable the aptamer of the polymer-aptamer conjugate to bind to the target polypeptide 24, creating a polypeptide-aptamer-polymer complex (block 36). Thus, the polymer-aptamer conjugate may function as a carrier during the purification process. In one embodiment, incubation may occur at approximately room temperature (e.g., 18° C.-30° C.). The polypeptide-aptamer-polymer complex is the portion of the solution that may precipitate from the aqueous mixture and may be isolated downstream in the method 30. After incubation, a block copolymer (e.g., pluronic) may be added to the mixture containing the polypeptide-aptamer-polymer complex as a solvent (block 38). The block copolymer may be an ethylene oxide (EO) block copolymer, a propylene oxide (PO) block copolymer, an EO/PO block copolymer, or any other suitable block copolymer.

The block copolymer may be a thermoresponsive polymer, as well, such that the physical properties of the block copolymer change with temperature. As previously discussed, the thermoresponsive characteristic of the block copolymer may be described using the lower critical solution temperature (LCST) or the cloud point. The LCST is the temperature below which the polymer may be miscible in solution. In this manner, at temperatures at or above the LCST, partial liquid miscibility of the polymer may occur. The cloud point is the temperature at which the polymer in solution may begin to phase-separate, thus having a cloudy appearance as two phases begin to appear. The block copolymer used as a solvent in the method 30 may have different chemical properties from the polymer used for the polymer-aptamer conjugate, and thus the polymer and the block copolymer may have different cloud points or LCSTs. The cloud point of a polymer may be dependent on concentration of the polymer, and thus in some embodiments, the cloud point of the block copolymer may be sensitive to concentration of the block copolymer. The block copolymer may have a cloud point less than 45° C. (e.g., human physiological temperature), may have a cloud point within the range of 21-45° C., and may have a cloud point with the range of 25-41° C. As shown below with reference to FIG. 4, block copolymers having cloud points within this temperature range may be effective in enabling liquid-separation (e.g., phase partitioning) of the polymer of the polymer-aptamer conjugate (e.g., pNIPAM) and/or the block copolymer. Examples of the block copolymer include polypropylene oxide 1000 (PPG 1000) having a cloud point of 31.5° C., Pluronic L31 having a cloud point of 36° C., polypropylene oxide 725 (PPG 725) having a cloud point of 39.5° C., and Pluronic 17R4 having a cloud point of 40.2° C.

Next, the solution containing the target polypeptide 24, the host cell waste or other contaminants, the polymer-aptamer conjugate, and the block copolymer may be heated to initiate the liquid-liquid polymer phase separation (block 40). In this heating step, the solution may be heated to a second temperature that is greater than the incubation temperature (e.g., first temperature) of block 36. Thus, the second temperature may be greater than 32° C., but lower than 45° C. This heating step may enable the solution to separate into two liquid phases, the aqueous phase 18 (e.g. aqueous supernatant) and the liquid polymer phase 20. The liquid polymer phase 20 may contain the polypeptide-aptamer-polymer complex and the aqueous phase 18 may contain the host cell waste (e.g., contaminants). In an embodiment, the polymer partitioning occurs in the absence of added salt (i.e., without salt additives). That is, the reaction buffers may not require the addition of salts, such as modified sodium salts, which is in contrast to other separation techniques that require the presence of salt additives. In an embodiment, the liquid polymer phase forms upon heating in an isotonic buffer (e.g. culture media, PBS, physiological saline, or a combination thereof). In some embodiments, the liquid polymer phase 20 may form at the bottom of the reaction tube with the aqueous phase 18 above the liquid polymer phase 20. However, in some embodiments, the liquid polymer phase 20 may form on top of the aqueous phase 18. Thus, method 30 may enable purification of the target polypeptide 24 based on phase separation properties or buoyancy of the polymers used in the method 30. In some embodiments, a third polymer species (e.g., polysaccharides) may be added to invert the phase-partitioning properties of the liquid polymer phase.

Next, the aqueous phase 18 may be extracted (block 42) or otherwise separated from the liquid polymer phase 20. Then, the liquid polymer phase 20 may be resuspended to dissolve the aptamer and break the connection between the aptamer and the target polypeptide 24 such that the aptamer and the target polypeptide 24 are no longer bound, i.e., to generate free unbound target polypeptide, and to elute the free unbound target polypeptide 24 from the solution (block 44). In some embodiments, the liquid polymer phase 20 may be resuspended in buffer that may include salt, chelator, or mixture of both to dissociate the aptamer and elute the target polypeptide 24 from the pNIPAM polymer, and the eluted target polypeptide 24 may be recovered. In some embodiments, other techniques may be used to dissociate the aptamer from the target polypeptide 24, such as change in pH above or below the pI of the target polypeptide or resuspension of the liquid polymer phase 20 in water. Thus, the method 30 may enable isolation of the target polypeptide 24 via a liquid-liquid extraction technique based on the phase separation properties of added the polymers. In some embodiments, the liquid polymer phase is dissolved at room temperature to elute the target polypeptide and the solution is re-heated to phase-separate the liquid polymer phase away from the target polypeptide now free and unbound in the resulting aqueous phase.

While the disclosed embodiment is discussed in the context of a biomanufacturing setting that includes reaction tanks, it should be understood that the disclosed techniques may also be implemented in the context of individual reaction tubes or other containers. To that end, the container 12 and/or the reaction vessel 16 may be implemented as part of a kit that provides the appropriate reagents for performing the method 10. In one embodiment, the reagents for generating an aptamer-polymer conjugate from a user-provided aptamer specific for a target of interest are provided as part of the kit. Further, the environmentally-responsive or thermoresponsive block copolymer (or monomers to form the block copolymer) may also be provided as part of such a kit. In one example, the polymer and the block copolymer are provided together and are selected such that the cloud point of the polymer and the cloud point of the block copolymer are sufficiently distinct to facilitate aptamer-target binding and subsequent liquid-liquid separation.

As provided herein, aptamers may refer to binding elements that specifically bind to a target molecule (e.g., a target polypeptide) through one or more binding sites. The aptamer may be a single stranded (DNA) aptamer, a single stranded ribonucleic acid (RNA) aptamer, a peptide nucleic acid (PNA) aptamer, or a combination of these types. In some embodiments, the aptamer may include modified nucleotides that increase the folding diversity of the aptamer. In a further embodiment, the aptamer may include chemical modifications or side-chain fusions that protect the aptamer from enzymatic or chemical degradation. Aptamers may also include peptide bonds rather than phosphodiester bonds.

In some embodiments, one or more aptamers may be conjugated with the polymer to bind more than one target molecule. In some embodiments, an aptamer is a "randomer" and comprises a randomized aptamer sequence. In some embodiments an aptamer comprises locked nucleic acid (LNA) modifications.

In other embodiments, the polymer conjugates may be with other affinity binders (e.g., nucleotide affinity binders, etc.). That is, the polymers as provided may be conjugated to binders other than aptamers. Further, the polymer-affinity binder conjugates may be formed in manner similar to the formation of the polymer-aptamer conjugates. In one example, polymer conjugates may include polypeptide affinity binders such as protein A.

As provided, target molecules are capable of being bound by aptamers for subsequent isolation. Target molecules may include oligonucleotides, small molecules, peptides, or polypeptides. In some embodiments, the target molecules may be the desired product, contaminants, the desired product associated with other molecules (e.g., histone-associated DNA). In one example, target molecules are produced using eukaryotic or prokaryotic cells in a production container 12 that includes feedstock. In one example, the target molecule is a polypeptide produced by a transformed mammalian cell line. The polypeptide may be a biopharmaceutical. In other embodiments, the target molecule is undesirable and the provided methods enable affinity-removal of the undesirable target molecule such that purification of the desired target is improved.

In certain embodiments, the liquid-liquid target isolation is performed without employing centrifugation or membrane filtration steps.

As provided herein, an environmentally-responsive polymer may be a polymer responsive to a change in one or more properties or parameters (e.g., a physical or chemical change in the environment), such as temperature, humidity, pH, conductivity, the wavelength or intensity of light, an electrical or magnetic field, ultrasonic wave, and the like, which results in a response. A thermoresponsive polymer may be a polymer that undergoes a change in solubility in response to a change in temperature. By way of example, a thermoresponsive polymer may be soluble at a temperature below the LCST of the polymer but may precipitate out of the solution upon heating the solution to a temperature higher than the LCST of the polymer.

As used herein, a molecular weight of a polymer may refer to the statistical average molecular weight of all the polymer chains in the sample and is calculated by dividing the total weight of all the polymer molecules in a sample by the total number of polymer molecules in a sample.

While certain polymers as provided herein may be homopolymers (polymerized from a single type of monomer) or co-polymeric, other polymers, e.g., the environmentally responsive polymer or the co-solvent or block polymer, may be provided as copolymers formed from two or more different types of monomers. The copolymers may be block copolymers formed from different monomers that form blocks of repeating units.

EXAMPLES

Example 1

Cloud-point Measurements of Polypropylene Glycols (PPG) and Block Copolymers Comprised of Ethylene Oxide (EO) and Propylene Oxide (PO) (EP/PO)

Block copolymers of propylene oxide (PO) and ethylene oxide (EO) and propylene oxide (EO/PO) are generally FDA-approved for industrial uses (e.g. Pluronics) and are known to generally exhibit switchable solution properties based on temperature (e.g., thermoresponsiveness). To characterize the cloud point temperature or lower critical solubility temperature (LCST) of selected block copolymers, turbidimetry studies were conducted across a temperature range of 10° C.-80° C. using a ramp rate of 1° C./minute on a Cary 300 Bio UV/visible spectrophotometer equipped with a 12-cell Peltier temperature controller. The block copolymers were diluted to 1% concentration in sterile PBS for these temperature studies and turbidity was monitored by optical density (OD).

Figure 3:
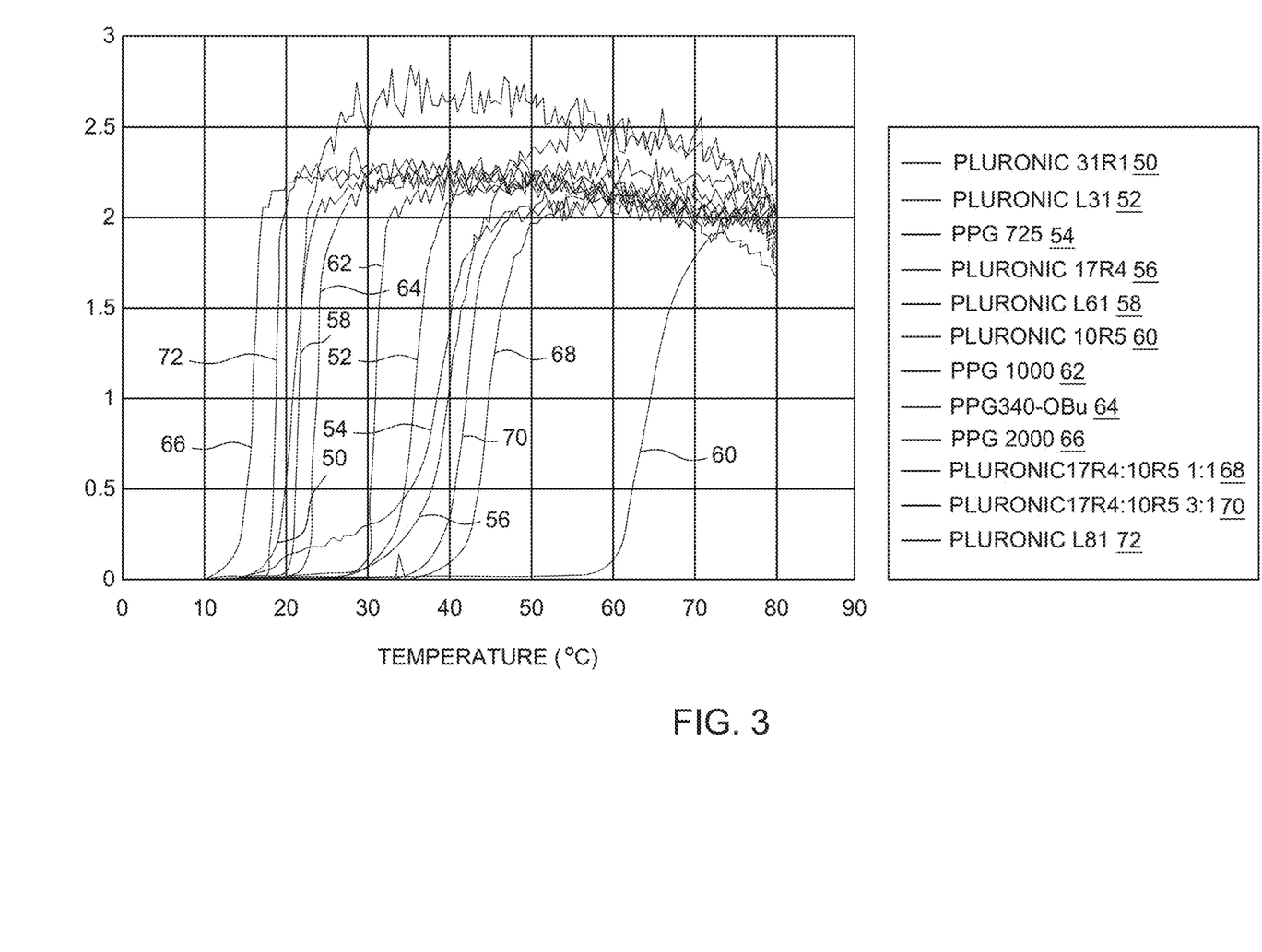
FIG. 3 is a graph showing cloud-point analysis of representative block copolymers, in accordance with aspects of the present disclosure.

FIG. 3 shows representative results for the selected PO and EO/PO block copolymers, and demonstrates that each block copolymer displays a unique cloud temperature inflection, reflecting a turbidity change from water-soluble to water-insoluble states (based on the optical density when the mixture begins to phase-separate). Polymer LCST may be estimated from the mid-point of each temperature inflection curve.

Example 2

Correlation of PPG and EO/PO LCST to Polymer-polymer Liquid-phase Partitioning of Thermoprecipitated pNIPAM at 40° C.

The selected thermoresponsive block copolymers comprised of PO and EO/PO, as described in example 1, were mixed with poly(N-isopropylacrylamide), (pNIPAM). The solutions were tested for the ability to solubilize thermoprecipitated pNIPAM and generate a liquid polymer phase above the LCST or cloud point of pNIPAM (e.g., >32° C.). For such testing, the thermoresponsive PO and EO/PO block copolymers were diluted to 20% concentration in PBS containing 25 mg/mL pNIPAM and the solution temperature was raised to 40° C.

Figure 4:
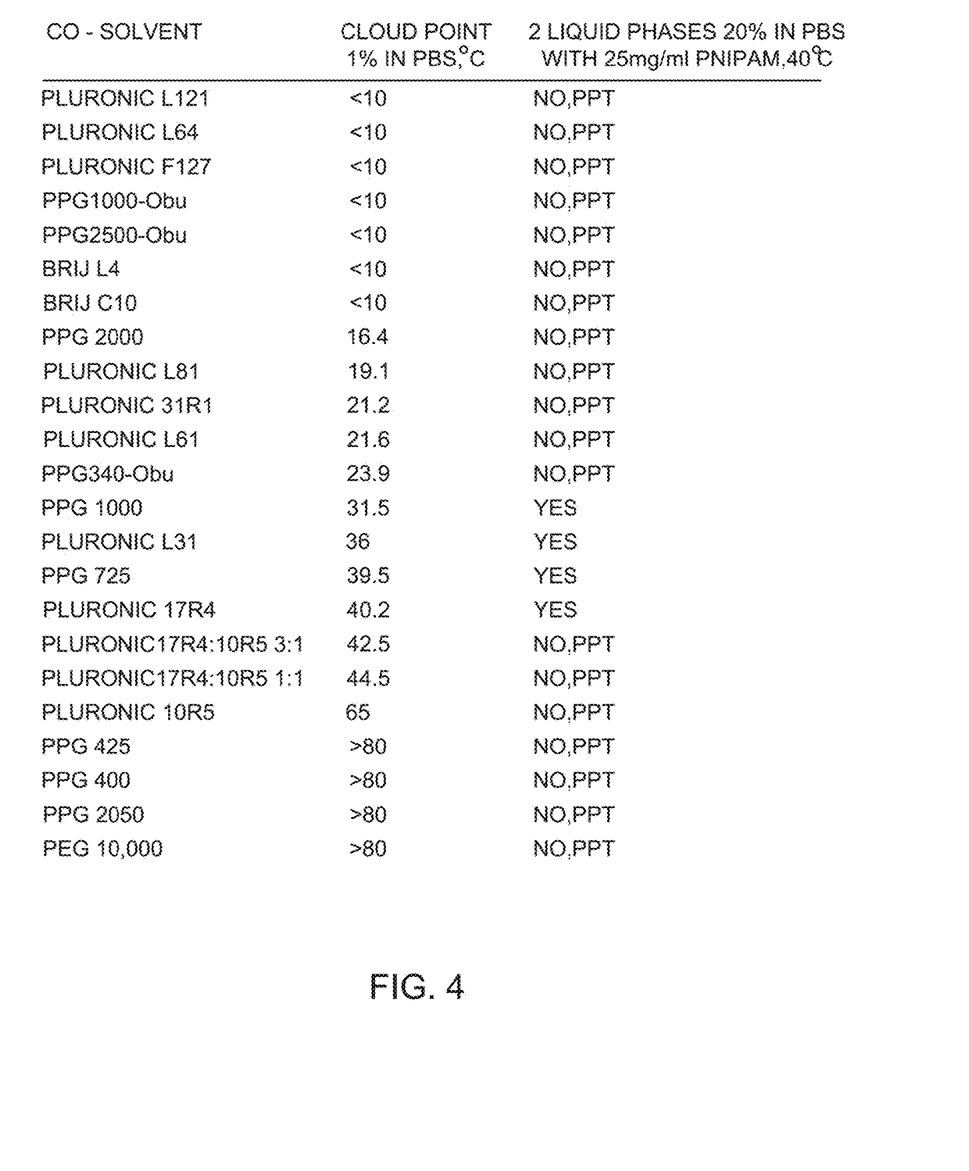
FIG. 4 shows liquid-liquid-phase separation results of the representative block copolymers of FIG. 3 in pNIPAM, in accordance with aspects of the present disclosure.

FIG. 4 summarizes the representative results of these studies. For the vast majority of the tested combinations, pNIPAM and/or the thermoresponsive PO/EO polymer formed an insoluble precipitate at 40° C. However, a two-phase liquid partition, having an aqueous phase and a liquid polymer phase, was observed when Pluronic L31, Pluronic 17R4, PPG 725, or PPG 1000 was mixed with pNIPAM and heated to 40° C. The liquid polymer phase was largely miscible and could be separated from the aqueous phase. A comparison of these observations against the LCSTs of the block copolymers, as described in example 1, illustrates that the use of EO/PO block copolymers with a cloud temperature greater than 24° C. (e.g., 25°-41° C.) enables the liquid-phase partitioning of thermoprecipitated pNIPAM such that the aqueous phase and the liquid polymer phase are produced. The upper cloud point or LCST range may be dependent on the experimental test condition (here set arbitrarily to 40° C.), however, for most biological applications, solution temperatures may be ideally less than 45° C. (e.g., human physiological temperature).

Example 3

Demonstration of Liquid-affinity Chromatography (e.g., Bioseparation) Using Polymer-polymer Liquid-phase Partitioning The polymer-aptamer conjugate was synthesized in the following manner. An IgE antibody-specific DNA aptamer sequence was synthesized using standard phosphoramidite chemistry and a non-nucleoside phosphoroamidite (comprising an ATRP initiator) was incorporated at 3' end of the DNA aptamer. Following HPLC purification, the DNA aptamer was used to co-initiate pNIPAM synthesis by ATRP. The pNIPAM (e.g., polymer) of target size >28 kD was synthesized in a 0.5 mL reaction volume using a mixture of two initiators, with the aptamer initiator comprising only 5 mole percent (1.4 mg), in the presence of 58 mg of monomer and copper catalyst. Sodium ascorbate (5 mM) was delivered at the same kinetic rate as the ATRP reaction to scavenge oxygen. At the completion of polymerization, copper catalyst was removed by centrifugal filtration over a size-selection membrane. The resulting polymer underwent three rounds of thermoprecipitation at 40° C. to remove unincorporated monomer, and the total aptamer content of the pNIPAM affinity polymer was measured at $OD_{260}$ nm on a NanoDrop.

Figure 5A:
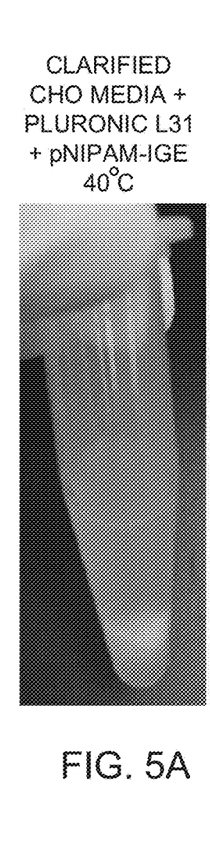
FIGS. 5A through 5E show separation products having two liquid phases, in accordance with aspects of the present disclosure.

The aptamer-conjugated pNIPAM affinity polymer (e.g., the polymer-aptamer conjugate) described above was then used to demonstrate liquid-affinity chromatography (e.g., bioseparation) using Pluronic L31 (e.g., the block copolymer) in the following manner. First, the pNIPAM affinity polymer was resuspended in 0.4 mL clarified CHO cell supernatant (from a culture density $>7\times10^6$ cells/mL). After thorough mixing at room temperature, 100 nM human IgE antibody (e.g., the target polypeptide) was spiked into the mixture of CHO cell supernatant and pNIPAM affinity polymer and subsequently incubated for 1 hour at room temperature to selectively bind antibody. The molar concentration of aptamer-pNIPAM was estimated to be approximately 10-fold greater than the spiked IgE antibody based on $OD_{260}$ nm readings. To phase-separate the triplex of antibody-aptamer-pNIPAM, approximately 80 mg of Pluronic L31 (e.g., the block copolymer) was added gravimetrically to the sample and mixed thoroughly. The combined solution was placed in an Eppendorf Thermomixer (40° C., 500 rpm) and heated for 10 minutes above the LCST of both pNIPAM and Pluronic L31. To speed-up and complete phase separation, the sample was briefly centrifuged (350xg) at 40° C. The bioseparation produced a top aqueous phase and a bottom liquid polymer phase, as shown in FIG. 5A. The top aqueous phase (e.g., supernatant) (S) having unbound material including CHO host cell protein (e.g., contaminant) was removed and saved (~0.2 mL). The bottom liquid polymer phase was resuspended in an equal volume (~0.2 mL) of 0.5 M NaCl to dissociate the aptamer and elute IgE antibody (e.g., the target polypeptide) from the pNIPAM affinity polymer. After thoroughly mixing the liquid polymer phase with 0.5 M NaCl, the eluted antibody was recovered by re-heating the solution to 40° C. for 10 minutes and collecting the top aqueous dissociation layer (D) after brief centrifugation in a pre-heated centrifuge (to accelerate phase separation). These top-collected fractions (S and D) were analyzed by SDS-PAGE and proteins were stained using SYPRO Ruby gel stain, as shown in FIG. 6.

Figure 5B:
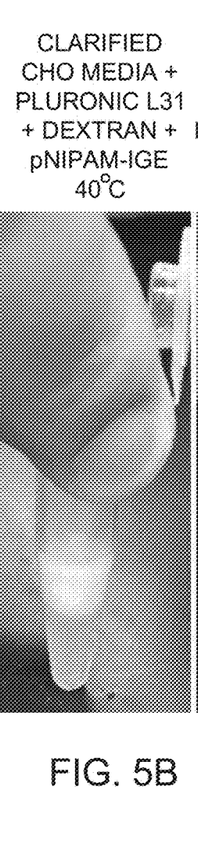
Figure 5C:
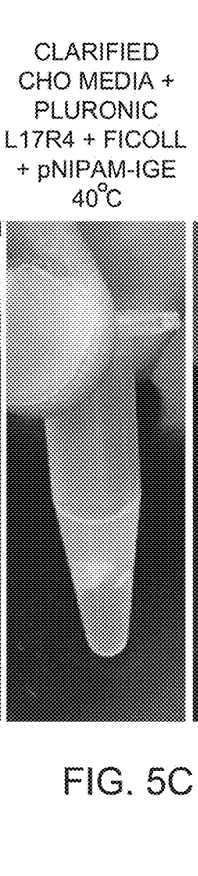

To reverse the phase order, the experiment above was repeated using 40mg of dextran along with 80 mg of Pluronic L31 to invert the liquid polymer layer to the top of the solution, as shown in FIG. 5B. Likewise, in another experiment, 40 mg of Ficoll was added along with 80 mg of Pluronic L17R4 to reverse the phase order and bring the liquid polymer layer to the top, as shown in FIG. 5C. Consequently, unbound aqueous phase (e.g., supernatant) (S) and aptamer dissociation eluate (D) fractions were collected from the bottom aqueous layers of each. These collected fractions (S and D) were analyzed by SDS-PAGE and proteins were stained using SYPRO Ruby gel stain, as shown in FIG. 6.

Figure 5D:
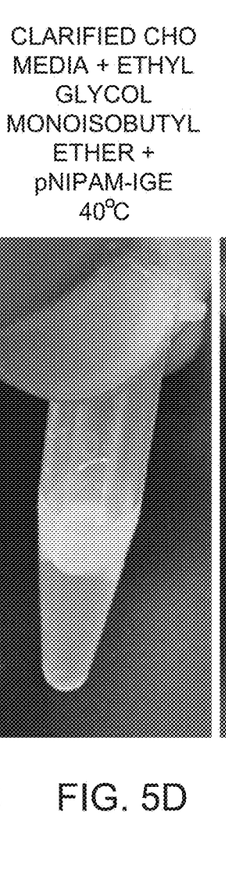
Figure 5E:
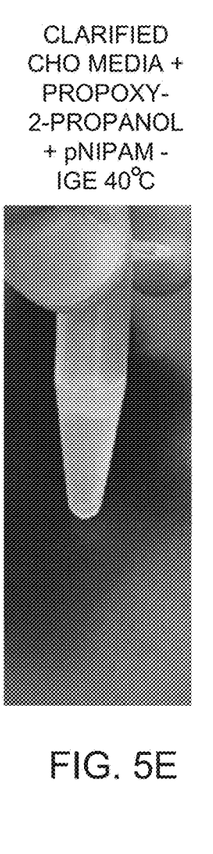

Lastly, the experiment was repeated using polar solvents to accomplish liquid-liquid extraction. Approximately 0.2 mL of ethyleneglycol mono-isobutyl ether or propoxy-2-propanol were substituted for Pluronic L31 in the detailed description provided above. After heating at 40° C., an organic phase formed at the top of this solution, as shown in FIGS. 5D and 5E respectively. Consequently, unbound aqueous phase (e.g., supernatant) (S) and aptamer dissociation eluate (D) fractions were collected from the bottom aqueous layers. These collected fractions (S and D) were analyzed by SDS-PAGE and proteins were stained using SYPRO Ruby gel stain, as shown in FIG. 6.

Figure 6:
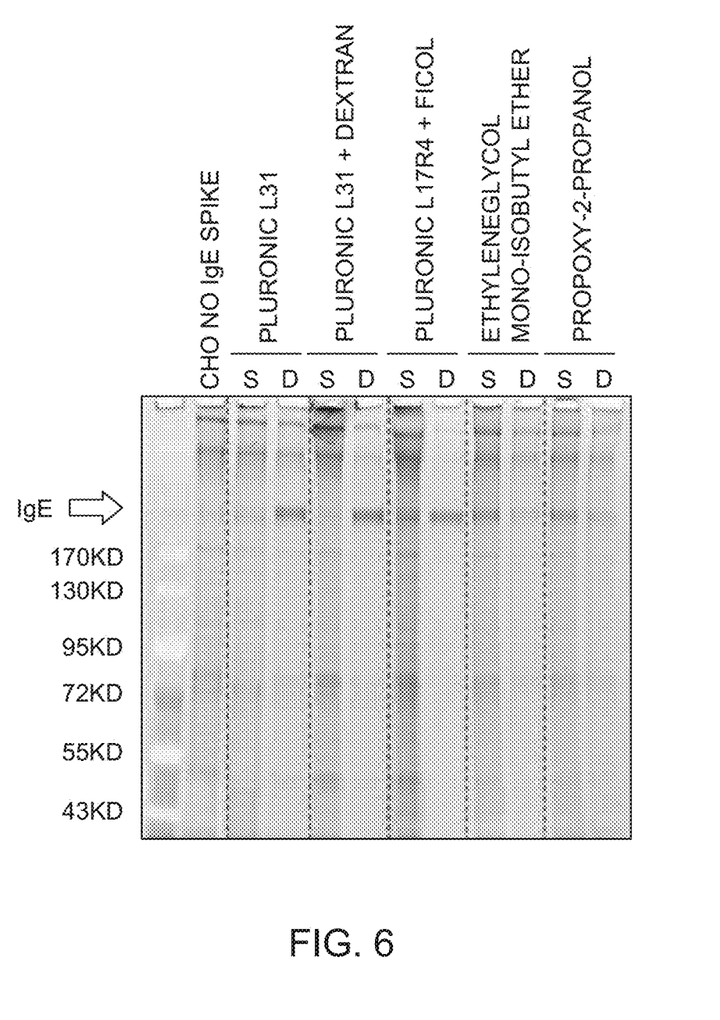
FIG. 6 shows a representative gel analysis of the two phases of each separation of FIG. 4, in accordance with aspects of the present disclosure.
Figure 7:
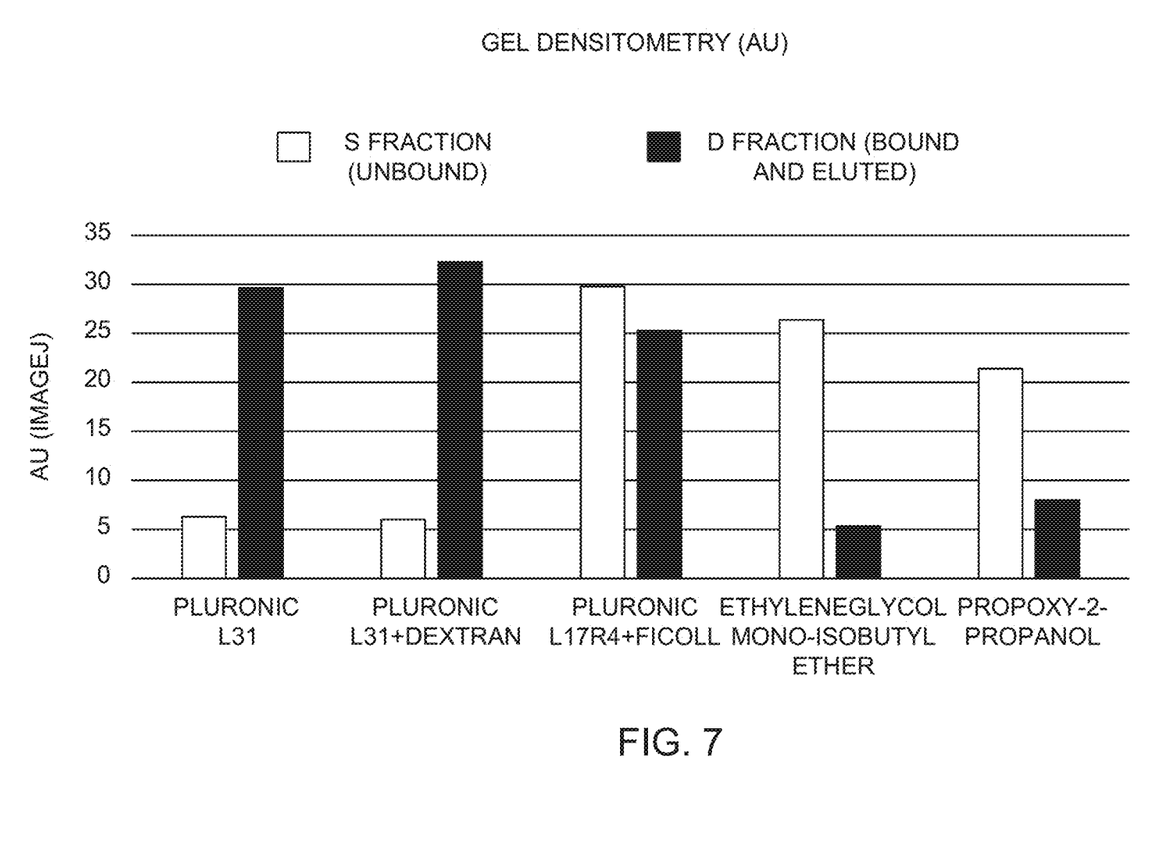
FIG. 7 is a graph illustrating the target polypeptide recovery of the two phases of each separation of FIG. 4, in accordance with aspects of the present disclosure.

FIG. 6 is an SDS-PAGE analysis of the resulting S (e.g. aqueous phase) and D (e.g., dissociated liquid polymer phase) fractions described above. IgE antibody (e.g., the target polypeptide) was efficiently captured and eluted from clarified CHO media using Pluronic L31 or L17R4 to solubilize the thermoprecipitated pNIPAM-affinity polymer into a liquid polymer phase. The liquid polymer phase formed either the top layer or the bottom layer of the solution, depending on co-addition of polysaccharides. The purity of IgE antibody (e.g., the target polypeptide) increased during the liquid affinity extraction by separating and withdrawing CHO host cell proteins (e.g., contaminants) to the aqueous phase supernatant fraction (S). In contrast, little to no IgE antibody capture was observed using the polar solvents ethyleneglycol mono-isobutyl ether or propoxy-2-propanol in combination with the pNIPAM affinity polymer. FIG. 7 further illustrates the antibody (e.g., target polypeptide) recovery from the aqueous phase (S) and liquid polymer phase (D) from each of the above referenced experiments. As shown, the binding and recovery of the antibody was greatest in the liquid polymer phase with the use of Pluronic L31 (e.g., the block copolymer) as a solvent in the liquid-liquid extraction.

Technical effects of the disclosed embodiments include a method of liquid-liquid extraction isolation of polypeptide-aptamer-polymer conjugates, and thus target polypeptides, that may be used in purification. In some embodiments, the method may include the addition of a polymer-aptamer conjugate to the target polypeptide (e.g., antibody) product of cell based biopharmaceutical production tanks. The polymer of the polymer-aptamer conjugate may be a thermo-responsive polymer and the aptamer may be a DNA aptamer. In some embodiments, the polymer may have a smaller molecular weight, thus enabling more efficient synthesis and ease of use of the polymer. The polymer-aptamer conjugate may bind to the target polypeptide, thus enabling an increase in the selectivity of the isolation method for the target productivity. In some embodiments, the isolation method may include addition of a thermoresponsive block co-polymer (e.g., pluronic) as a co-solvent to separate the solution into two liquid phases, an aqueous phase and a liquid polymeric phase. The cloud point or LCST of the thermoresponsive block co-polymer may be within a particular range (e.g., 25-41° C.), thus enabling the bioseparation of the aqueous phase containing contaminants of the target polypeptide production process and the liquid polymeric phase containing the target polypeptide. The liquid-liquid extraction isolation method may enable the target polypeptide to be separated, extracted, and isolated from contaminants using a simple to run technique by utilizing the selective binding of the aptamer and the thermoreactive nature of the polymer and the block copolymer. The liquid-liquid extraction isolation method may, thus, enable an increase in the efficiency and selectivity of purification of target biopharmaceutical products from solution. However, in some embodiments, the aptamer may be specific to one or more contaminant species and the liquid-liquid extraction isolation method may, thus, enable the depletion of undesirable contaminants, thereby improving purification of a target biopharmaceutical product by reducing background.

This written description uses examples to disclose the concepts discussed herein, including the best mode, and also sufficient disclosure to enable any person skilled in the art to practice the disclosure, including making and using any devices or systems and performing any incorporated methods. The patentable scope of the disclosure is defined by the claims, and may include other examples that occur to those skilled in the art such as polymer conjugates comprising polypeptide affinity binders. Such other examples are intended to be within the scope of the claims if they have structural elements that do not differ from the literal language of the claims, or if they include equivalent structural elements with insubstantial differences from the literal languages of the claims.

The invention claimed is:

1. A method for purification of a target in a solution, comprising:
    providing a target in a solution, the solution comprising one or more contaminants;
    providing a polymer conjugate in the solution, wherein the polymer conjugate is configured to specifically bind the target;
    incubating the solution at a first temperature to facilitate binding of the polymer conjugate to the target;
    providing an environmentally-responsive block copolymer in the solution, wherein the environmentally-responsive block copolymer comprises one or more of an ethylene oxide (EO) block copolymer, a propylene oxide (PO) block copolymer, or an EO/PO block copolymer;
    heating the solution comprising the environmentally-responsive block copolymer and the polymer conjugate bound to the target at a second temperature to initiate a liquid-liquid phase separation, wherein the liquid-liquid phase separation produces an aqueous phase and a liquid polymer phase, and wherein the liquid polymer phase comprises the polymer conjugate bound to the target;
    separating the aqueous phase from the liquid polymer phase;
    treating the liquid polymer phase such that the target dissociates from the polymer conjugate to generate unbound target; and
    eluting the unbound target, wherein the unbound target is substantially isolated from the liquid polymer phase after the eluting.

2. The method of claim 1, wherein the environmentally-responsive block copolymer is a thermoresponsive block copolymer.

3. The method of claim 2, wherein the thermoresponsive block copolymer has a cloud point between 21° C. and 45° C.

4. The method of claim 1, wherein the polymer conjugate comprises an aptamer.

5. The method of claim 1, wherein the polymer of the polymer conjugate is poly(N-isopropylacrylamide) (pNIPAM).

6. The method of claim 1, wherein the target is selected from one or more of a contaminant and a biotherapeutic protein.

7. The method of claim 1, wherein the environmentally-responsive block copolymer comprises one or more of 1000 average molecular weight polypropylene oxide (PPG 1000), 1100 average molecular weight non-ionic tri-block poly(ethylene glycol)-block-poly(propylene glycol)-block-poly(ethylene glycol) copolymer (Pluronic L31), 725 average molecular weight polypropylene oxide (PPG 725), and 2700 average molecular weight triblock Poly(propylene glycol)-block-poly(ethylene glycol)-block-poly(propylene glycol) copolymer (Pluronic 17R41).

8. The method of claim 1, wherein the polymer of the polymer conjugate is a thermoresponsive polymer, wherein a cloud point of the polymer of the polymer conjugate is different than a cloud point of the environmentally-responsive block copolymer.

9. The method of claim 1, wherein the second temperature is higher than the first temperature, and wherein the second temperature is lower than 45° C.

10. A method for selective purification of a target in a solution, comprising:
   binding a target to an aptamer of a polymer-aptamer conjugate in a solution, wherein the aptamer of the polymer-aptamer conjugate is configured to specifically bind the target;
   separating the solution into two liquid phases using a thermoresponsive block copolymer, wherein the thermorepsonsive block copolymer is one of an ethylene oxide (EO) block copolymer, a propylene oxide (PO) block copolymer, or an EO/PO block copolymer, wherein the thermoresponsive block copolymer has a cloud point between 25° C. and 41° C., and wherein the two liquid phases comprise an aqueous phase and a liquid polymer phase, and wherein the liquid polymer phase comprises the target bound to the polymer-aptamer conjugate;
   extracting the aqueous phase from the liquid polymer phase;
   treating the liquid polymer phase such that the target dissociates from the polymer-aptamer conjugate to generate unbound target; and
   eluting the target.

11. The method of claim 10, comprising incubating the solution containing the target and the polymer-aptamer conjugate at a first temperature to facilitate target binding.

12. The method of claim 11, comprising heating the solution containing the target bound to the polymer-aptamer conjugate and the thermoresponsive block copolymer to a second temperature to initiate the separating, wherein the second temperature is higher than the first temperature.

13. The method of claim 10, wherein the target is selected from one or more of a contaminant and a biotherapeutic protein.

14. The method of claim 10, wherein the polymer of the polymer-aptamer conjugate is a thermoresponsive polymer, wherein a cloud point of the polymer of the polymer-aptamer conjugate is different than the cloud point of the environmentally-responsive block copolymer.

15. The method of claim 10, wherein the target bound to the polymer-aptamer conjugate is not in the aqueous phase after the separating.

16. A method for selective purification of a target in a solution, comprising:
   adding a polymer-aptamer conjugate to a solution comprising a target, wherein the polymer-aptamer conjugate is configured to bind the target, wherein the polymer of the polymer-aptamer conjugate comprises a thermoresponsive polymer having a first cloud point, and wherein the aptamer of the polymer-aptamer conjugate comprises a DNA aptamer;
   incubating the solution at a first temperature to facilitate binding of the polymer-aptamer conjugate to the target;
   adding a thermoresponsive block copolymer to the solution, wherein the thermoresponsive block copolymer is one of an ethylene oxide (EO) block copolymer, a propylene oxide (PO) block copolymer, or an EO/PO block copolymer and has a second cloud point between 25° C. and 41° C.; and
   heating the solution at a second temperature to initiate a first liquid-liquid phase separation, wherein the second temperature is higher than the first temperature, wherein the first liquid-liquid phase separation produces a first aqueous phase and a first liquid polymer phase, wherein the first aqueous phase comprises unbound species, and wherein the first liquid polymer phase comprises the target bound to the polymer-aptamer conjugate.

17. The method of claim 16, further comprising:
   extracting the aqueous phase from the liquid polymer phase;
   reducing heat of solution to a third temperature, wherein the third temperature is lower than the cloud point of the of the thermoresponsive block copolymer;
   adding a buffer to the solution, wherein the buffer is configured to unbind the polymer-aptamer conjugate from the target to produce an unbound target;
   heating the solution to a fourth temperature to initiate a second liquid-liquid phase separation, wherein the second liquid-liquid phase separation produces a second aqueous phase and a second liquid polymer phase, wherein the second aqueous phase comprises the unbound target, and wherein the second liquid polymer phase comprises the polymer-aptamer conjugate;
   removing the second liquid polymer phase; and
   eluting the unbound target from the second aqueous phase.

18. The method of claim 16, wherein the thermoresponsive block copolymer comprises one of 1000 average molecular weight polypropylene oxide (PPG 1000), 1100 average molecular weight non-ionic tri-block poly(ethylene glycol)-block-poly(propylene glycol)-block-poly(ethylene glycol) copolymer (Pluronic L31), 725 average molecular weight polypropylene oxide (PPG 725), and 2700 average molecular weight triblock Poly(propylene glycol)-block-poly(ethylene glycol)-block-poly(propylene glycol) copolymer (Pluronic 17R41).

\* \* \* \* \*